US007852564B2

(12) United States Patent
Messina

(10) Patent No.: US 7,852,564 B2
(45) Date of Patent: Dec. 14, 2010

(54) DEVICES AND/OR SYSTEMS FOR ILLUMINATING A COMPONENT

(75) Inventor: Michael C. Messina, Hooksett, NH (US)

(73) Assignee: Microscan Systems, Inc., Renton, WA (US)

(*) Notice: Subject to any disclaimer, the term of this patent is extended or adjusted under 35 U.S.C. 154(b) by 301 days.

(21) Appl. No.: 11/904,227

(22) Filed: Sep. 26, 2007

(65) Prior Publication Data

US 2008/0131111 A1    Jun. 5, 2008

Related U.S. Application Data

(60) Provisional application No. 60/847,590, filed on Sep. 27, 2006.

(51) Int. Cl.
*G02B 27/14* (2006.01)
(52) U.S. Cl. .................. 359/629; 362/346
(58) Field of Classification Search ................ 359/618, 359/850, 629; 362/241, 243, 296.01, 297, 362/341, 346; 396/182, 200
See application file for complete search history.

(56) References Cited

U.S. PATENT DOCUMENTS

| | | | |
|---|---|---|---|
| 5,298,989 A * | 3/1994 | Tsukahara et al. .......... 348/126 |
| 5,461,417 A | 10/1995 | White |
| 5,539,485 A | 7/1996 | White |
| 5,604,550 A | 2/1997 | White |
| 5,684,530 A | 11/1997 | White |
| 5,761,540 A | 6/1998 | White |
| 6,059,421 A * | 5/2000 | White et al. ............... 362/97.1 |
| 6,191,850 B1 | 2/2001 | Chiang |
| 6,667,762 B1 | 12/2003 | Bouvier et al. |
| 6,829,852 B1 | 12/2004 | Uehran |
| 2002/0076096 A1 | 6/2002 | Silber et al. |
| 2002/0167645 A1 | 11/2002 | Johnson |
| 2002/0191102 A1 | 12/2002 | Yuyama et al. |
| 2003/0053307 A1 | 3/2003 | Talamo et al. |
| 2004/0174591 A1 | 9/2004 | Sander |
| 2006/0103903 A1 | 5/2006 | Thomas |
| 2006/0228018 A1 | 10/2006 | Abramovich |
| 2007/0176848 A1 | 8/2007 | Ferren |
| 2008/0106794 A1 | 5/2008 | Messina |

FOREIGN PATENT DOCUMENTS

| | | |
|---|---|---|
| EP | 0 446 838 A | 9/1991 |
| WO | WO 99/20048 | 4/1999 |

(Continued)

OTHER PUBLICATIONS

International Search Report, PCT/US2007/021034, mail date Apr. 21, 2008.

(Continued)

*Primary Examiner*—Joseph Martinez
(74) *Attorney, Agent, or Firm*—Blakely Sokoloff Taylor & Zafman LLP

(57) ABSTRACT

Certain exemplary embodiments can comprise a system, which can comprise a beamsplitter. The beamsplitter can comprise at least three distinct light reflection zones. Each zone of the three distinct light reflection zones can be adapted to cause light from one or more light sources to be reflected at a different angle relative to an axis of a camera.

45 Claims, 6 Drawing Sheets

FOREIGN PATENT DOCUMENTS

| WO | WO99/20048 | * | 4/1999 |
|---|---|---|---|
| WO | WO 2008/039462 A2 | | 4/2008 |

OTHER PUBLICATIONS

Written Opinion of the International Searching Authority, International Application No. PCT/US2007/021034, mail date Apr. 21, 2008.

U.S. Appl. No. 11/903,332, filed Sep. 21, 2007, Messina.

U.S. Appl. No. 11/903,335, filed Sep. 21, 2007, Messina et al.

PCT/US2007/020695, International Search Report and Written Opinion of the International Searching Authority, mail date Apr. 16, 2008.

PCT/US2007/020695, International Preliminary Report on Patentability, date of issuance Mar. 31, 2009.

PCT/US2007/021034, International Preliminary Report on Patentability, date of issuance Mar. 31, 2009.

* cited by examiner

5000

```
┌─────────────────────────────────┐
│   Fabricate beamsplitter        │ 5100
└─────────────────────────────────┘
              │
              ▼
┌─────────────────────────────────┐
│   Assemble system               │ 5200
└─────────────────────────────────┘
              │
              ▼
┌─────────────────────────────────┐
│   Illuminate first subset of lights │ 5300
└─────────────────────────────────┘
              │
              ▼
┌─────────────────────────────────┐
│   Obtain image                  │ 5400
└─────────────────────────────────┘
              │
              ▼
┌─────────────────────────────────┐
│   Determine second subset of lights │ 5500
└─────────────────────────────────┘
              │
              ▼
┌─────────────────────────────────┐
│   Illuminate determined lights  │ 5600
└─────────────────────────────────┘
              │
              ▼
┌─────────────────────────────────┐
│   Obtain image                  │ 5700
└─────────────────────────────────┘
```

Fig. 5

DEVICES AND/OR SYSTEMS FOR ILLUMINATING A COMPONENT

CROSS-REFERENCES TO RELATED APPLICATIONS

This application claims priority to, and incorporates by reference herein in its entirety, pending U.S. Provisional Patent Application Ser. No. 60/847,590, filed 27 Sep. 2006.

BACKGROUND

Objects can be illuminated for camera imaging and/or machine vision applications via a light source. The light energy from the light source can be partially reflected onto a surface of an object via a beamsplitter. Output from the light source that reflects from a surface of the object can be dependent on geometry and/or determined via raytracing. Light energy that does not reflect off of the beamsplitter can define non-uniformities of the surface of the object. Improved devices, systems, and/or methods for illumination can be desirable for certain applications.

SUMMARY

Certain exemplary embodiments comprise a system, which can comprise a beamsplitter. The beamsplitter can comprise at least three distinct light reflection zones. Each zone of the three distinct light reflection zones can be adapted to cause light from one or more light sources to be reflected at a different angle relative to an axis of a camera.

BRIEF DESCRIPTION OF THE DRAWINGS

A wide variety of potential practical and useful embodiments will be more readily understood through the following detailed description of certain exemplary embodiments, with reference to the accompanying exemplary drawings in which:

FIG. 5 is a flowchart of an exemplary embodiment of a method 5000; and

DETAILED DESCRIPTION

Certain exemplary embodiments provide a system, which can comprise a beamsplitter. The beamsplitter can comprise at least three distinct light reflection zones. Each zone of the three distinct light reflection zones can be adapted to cause light from one or more light sources to be reflected at a different angle relative to an axis of a camera.

A machine vision system and/or imaging system can utilize a set of lighting elements, such as light emitting diodes (LEDs) to illuminate a component and/or portions of the component. A camera of the system can be disposed such that the camera lens can be pointed toward the component along a camera axis.

The set of lighting elements can be arranged in an array behind a diffuser. The lighting elements and diffuser can direct light in a primary illumination direction that can be substantially perpendicular to the camera axis. Light from the set of lighting elements can pass through the diffuser, which can diffuse the light to improve illumination uniformity. The diffused light can be directed toward a non-planar beamsplitter, which can allow some of the light to pass to a camera side of the beamsplitter. The non-planar beamsplitter can cause a portion of the light to be reflected onto a surface of the component. The non-planar beamsplitter can provide at least three distinct zones of reflection. Each zone of reflection can causes light from the set of lighting elements to be reflected at a different angle and/or can provide increased angular lighting coverage as compared to a single non-planar beamsplitter. Multiple zones of reflection can cause an increased quantity of light to be reflected by the beam splitter for illumination of the component as compared to a single zone of reflection of a substantially planar beamsplitter. The beamsplitter can cause light reflected from the component to be partially reflected and directed to the diffuser. Rays of light that reflect from the component and are not reflected by the beamsplitter to the diffuser can pass through the beamsplitter and allow an image of the component to be available to the camera. Some beamsplitters can utilize substantially planar segments to define the zones. Other beamsplitters can utilize non-planar segments and/or curved surfaces to define the zones.

Figure 1:
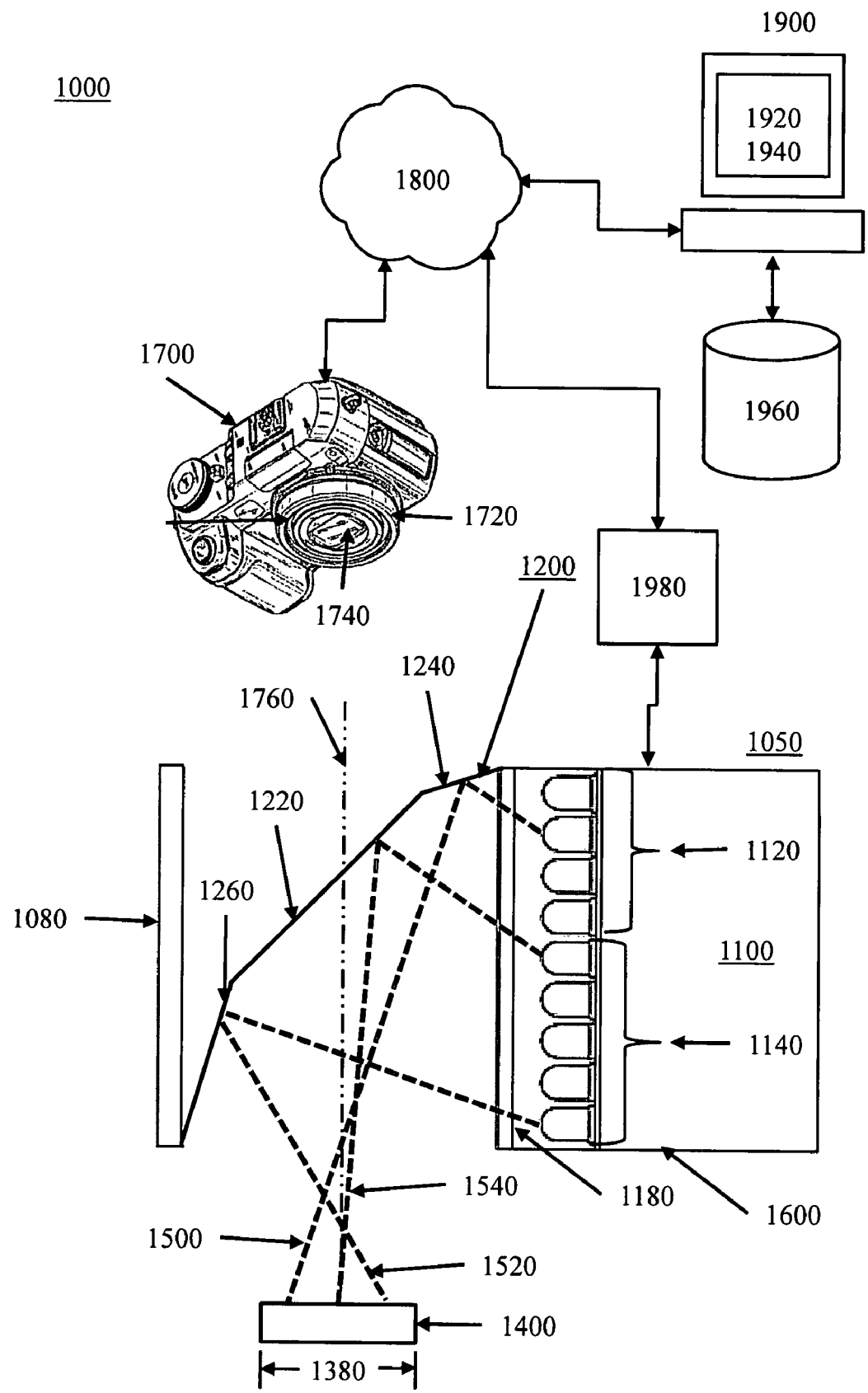
FIG. 1 is a block diagram of an exemplary embodiment of a system 1000.

FIG. 1 is a block diagram of an exemplary embodiment of a system 1000, which can comprise a set of light sources 1100. Set of light sources 1100 can be adapted to illuminate a component 1400 via light energy passed through a diffuser 1180. Diffuser 1180 can be located in a light path between set of light sources 1100 and a beamsplitter 1200. Light energy passing through diffuser 1180 can be transmitted to beamsplitter 1200, which can comprise at least three distinct light reflection zones, such as a first light reflection zone 1220, a second light reflection zone 1240, and a third zone 1260. Each zone of first light reflection zone 1220, second light reflection zone 1240, and third light reflection zone 1260 can be adapted to cause light from one or more light sources, such as set of light sources 1100, to be reflected at a different angle relative to an axis 1760 of a camera and/or Machine Vision system 1700. Beamsplitter 1200 can be adapted to cause component 1400 to be illuminated via light energy reflected from each of first light reflection zone 1220, second light reflection zone 1240, and/or third light reflection zone 1260. One or more of first light reflection zone 1220, second light reflection zone 1240, and third light reflection zone 1260 can comprise a substantially planar portion.

First light reflection zone 1220, second light reflection zone 1240, and third light reflection zone 1260 can be made, assembled, and/or fabricated as a single unitary device. In certain exemplary embodiments, first light reflection zone 1220, second light reflection zone 1240, and third zone 1260 can be assembled from two or more distinct and/or separate pieces. Set of light sources 1100 can comprise a first subset of light sources 1120 and a second subset of light sources 1140. Camera and/or Machine Vision system 1700 can be adapted to capture an image of component 1400, which can be illuminated by set of light sources 1100. Camera and/or Machine Vision system 1700 can be adapted to capture an image of component 1400. A lens 1740 of camera and/or Machine Vision system 1700 can be facing component 1400 along an axis 1760 of camera and/or Machine Vision system 1700. Camera and/or Machine Vision system 1700 can be adapted to interpret an obtained image of component 1400 illuminated by set of light sources 1100. While three zones are illustrated in beamsplitter 1200 in the exemplary embodiment of system 1000, beamsplitter 1200 can comprise any number of distinct zones and/or can have one or more curved portions. For example, a plurality of zones of beamsplitter 1200 can comprise a fourth distinct zone.

Camera and/or Machine Vision system 1700 can be communicatively coupled to information devices via a network 1800. For example, image information can be transmitted from camera and/or Machine Vision system 1700 to an information device 1900. Information device 1900 can comprise a user interface 1920, a user program 1940, and a memory device 1960. User program 1940 can be adapted to process image information received from camera and/or Machine Vision system 1700. User interface 1920 can be adapted to render information regarding user program 1940 and/or image information obtained from camera and/or Machine Vision system 1700. Memory device 1960 can be adapted to store image information and/or information related to controlling set of light sources 1100.

A light controller 1980, which can comprise a processor, can control the set of light sources 1100. Light controller 1980 can be adapted to turn on and turn off any subset of the set of light sources 1100. For example, light controller 1980 can be adapted to turn on and off first subset of light sources 1120 without turning on second subset of light sources 1140. Light controller 1980 can be adapted to turn on and off second subset of light sources 1140 without turning on first subset of light sources 1120. While two subsets of light sources are illustrated in system 2000, certain exemplary embodiments can comprise any count of subsets up to and including a count of subsets of light sources that is approximately equal to a count of light sources. Light controller 1980 can be adapted to change an intensity of one or more light sources of set of light sources 1100. Thereby, light controller 1980 can be adapted to provide light energy, which can be partially reflected via first light reflection zone 1220, a second light reflection zone 1240, and a third light reflection zone 1260. Light controller 1980 can receive information from, for example, a light meter, camera and/or Machine Vision system 1700, and/or information device 1900, which can be utilized to determine which light sources of the set of light sources 1100 to illuminate, and/or an intensity of any light sources illuminated, during any particular time interval.

In certain exemplary embodiments, beamsplitter 1200 can be segmented and can be adapted to reflect light rays at a plurality of angles. For example, first light reflection zone 1220 can be adapted to reflect light rays 1540 at an angle such as the illustrated exemplary angle shown for light rays 1540. Second light reflection zone 1240 can be adapted to reflect light rays 1500 at an angle such as the illustrated exemplary angle shown for light rays 1500. Third light reflection zone 1260 can be adapted to reflect light rays 1520 at an angle such as the illustrated exemplary angle shown for light rays 1520. Utilizing system 1000, a component 1400 can be illuminated with light energy transmitted via diffuser 1180 and reflected via beamsplitter 1200 in a determined and/or relatively uniform manner. Certain exemplary embodiments can provide an imaging path with relatively low distortion.

Dimensions of system 1000 can be based upon a diameter 1720 of a lens 1740 and/or a viewing aperture of camera and/or Machine Vision system 1700. Dimensions and/or relationships between dimensions illustrated in system 1000 are exemplary and not restrictive. Dimensions and/or characteristics of system 1000 and/or elements thereof can vary over a wide range and can be determined and/or established by those skilled in the art. In certain exemplary embodiments Dimensions and/or characteristics of system 1000 can be established by two-dimensional raytracing. In certain exemplary embodiments:

- a chamber 1050 can be adapted to house and/or support beamsplitter 1200;
- a wall 1080 of chamber 1050 can be a substantially light absorbing wall such that light passing from light sources 1100 via diffuser 1180 through beamsplitter 1200 is not substantially reflected from wall 1080 to lens 1740 of camera and/or Machine Vision system 1700;
- a diameter 1380 of component 1400 can be approximately equal to diameter 1720 of a lens 1740 of camera and/or Machine Vision system 1700;
- a substantially vertical distance between chamber 1050 and component 1400 can be approximately equal to diameter 1380 of component 1400;
- system 1000 can be a Diffuse On-Axis Light (DOAL) system;
- the diameter 1720 of lens 1740 of camera and/or Machine Vision system 1700 imaging component 1400 can result in an image path that is approximately equal to diameter 1380 of component 1400;
- a height of chamber 1050 can be greater than approximately two times the diameter 1380 of component 1400;
- a width of an approximate half portion of chamber 1050 can be approximately equal to diameter 1380 of component 1400;
- a width of chamber 1050 can be approximately two times diameter 1380 of component 1400;
- beamsplitter 1200 can be operatively mounted in a substantially rectangular chamber 1050, a cross-section of chamber 1050 can have an approximate width that is approximately two times the diameter 1380 of component 1400;
- component 1400 can be adapted to be photographed by camera and/or Machine Vision system 1700; and/or
- diameter 1720 of lens 1740 of camera and/or Machine Vision system 1700 can be approximately equal to a closest distance from a plane 1600, defined by a bottom edge 1600 of chamber 1050 of system 1000, and component 1400.

Figure 2:
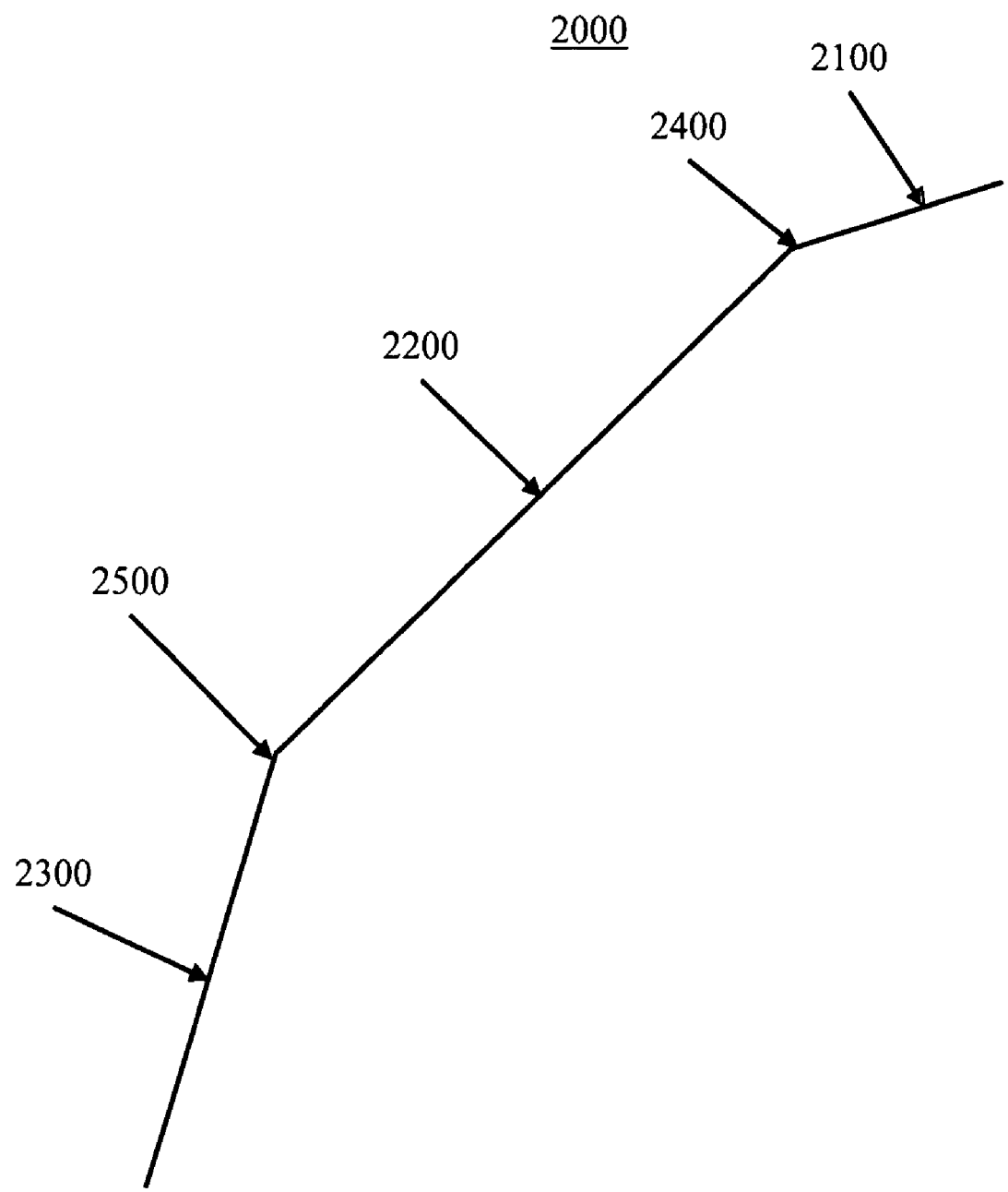
FIG. 2 is a block diagram of an exemplary embodiment of a beamsplitter 2000.

FIG. 2 is a block diagram of an exemplary embodiment of a beamsplitter 2000, which can comprise a first light reflection zone 2100, a second light reflection zone 2200, and a third light reflection zone 2300. In certain exemplary embodiments, beamsplitter 2000 can be a single piece of substantially unitary construction. In certain exemplary embodiments, beamsplitter 2000 can comprise a plurality of segments joined and/or fused together at joint 2400 and/or joint 2500. The illustrated embodiment of system 2000 can be varied in alternative applications, which can dynamically affect related parameters in operative embodiments. Segments that lie outside of an imaging path segment can be made of numerous different materials such as a beamsplitter material, mirror material, and/or reflective film, and can have varying and/or partial reflectivity (e.g., flat glass, plastic, polished metal).

Figure 3:
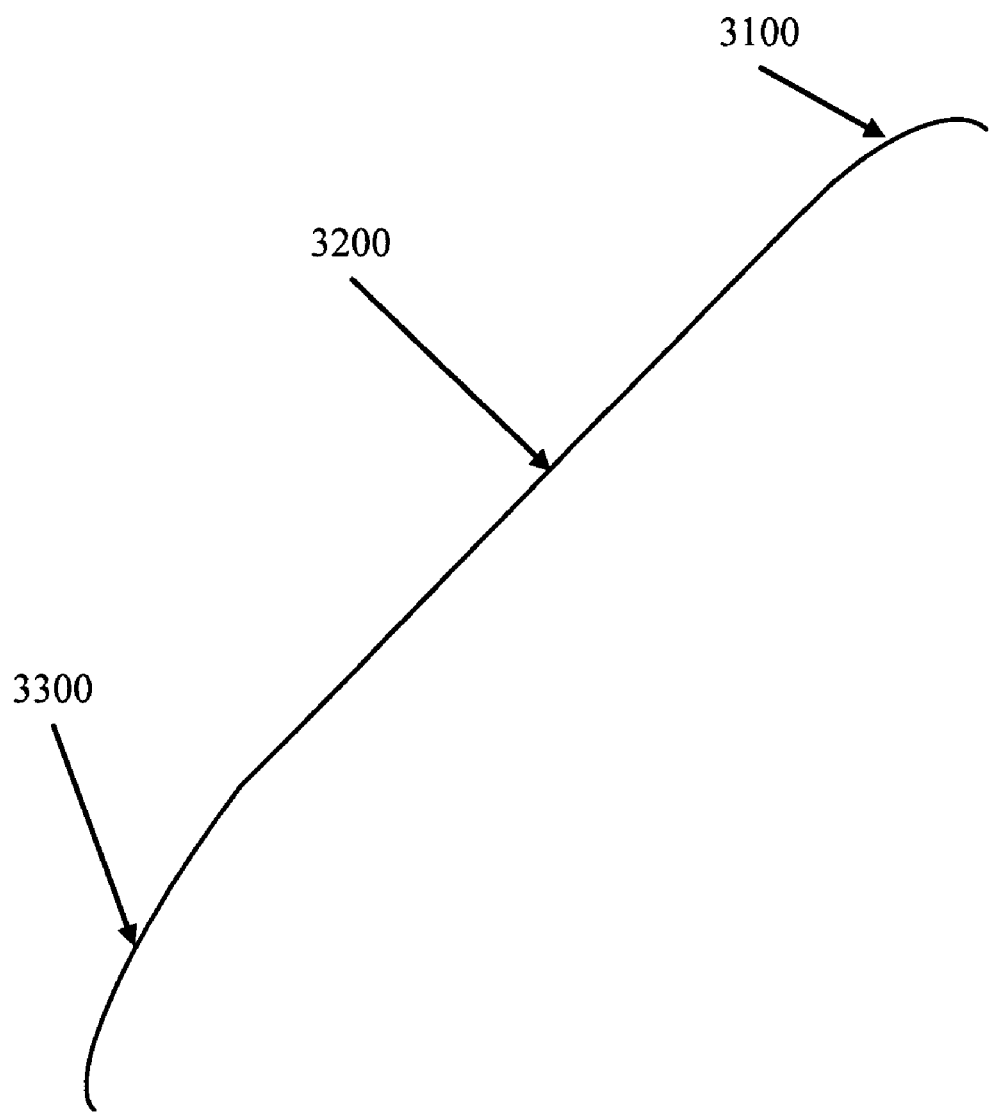
FIG. 3 is a block diagram of an exemplary embodiment of a beamsplitter 3000.

FIG. 3 is a block diagram of an exemplary embodiment of a beamsplitter 3000, which can comprise a first light reflection zone 3100, a second light reflection zone 3200, and a third light reflection zone 3300. Certain exemplary embodiments of beamsplitter 3000 can comprise curved portions, such as the illustrated curved portions of first light reflection zone 3100 and third light reflection zone 3300. In certain exemplary embodiments, geometry outside of the imaging path can also vary by having flat and/or curved surfaces to enhance a uniformity of reflected light. In certain exemplary embodiments, at least one portion disposed between a pair of at least three distinct zones can be curved, such as the illustrated curved portions of first light reflection zone 3100 and third light reflection zone 3300.

Figure 4:
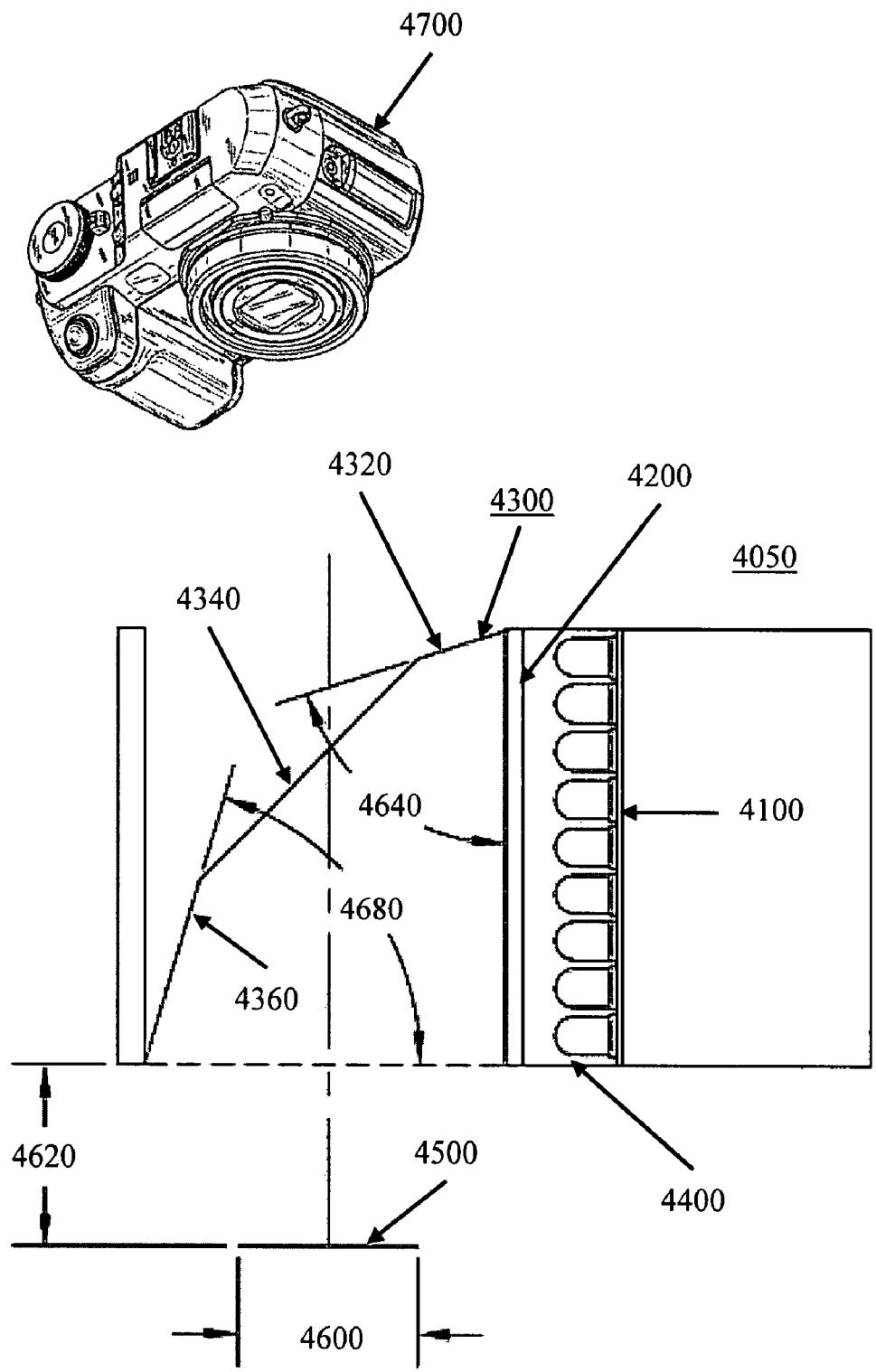
FIG. 4 is a block diagram of an exemplary embodiment of a system 4000.

FIG. 4 is a block diagram of an exemplary embodiment of a system 4000, which can comprise a plurality of light sources 4100 and a camera 4700. In certain exemplary embodiments, light sources 4100 can comprise an array of Light Emitting Diodes (LEDs) populated on a circuit board, incandescent bulbs, fiber optically transmitted light sources from remotely located sources, electro-luminescent panels, and/or mini fluorescent bulbs, etc. Light energy emitted from plurality of light sources 4100 can be diffused via a diffuser 4200. The diffused light energy can be at least partially reflected via beamsplitter 4300 to illuminate a component 4500.

Beamsplitter 4300 can comprise a first light reflection zone 4320, a second light reflection zone 4340, and a third light reflection zone 4360. In the exemplary embodiment illustrated, a plane defined first reflection zone 4320 can intersect with a plane defined by diffuser 4200 at an angle 4640. In the exemplary embodiment illustrated, a plane defined third reflection zone 4360 can intersect with a plane defined by a chamber bottom 4400 at an angle 4680. Angle 4640 and/or angle 4680 can be, in degrees, approximately 35, 39.1, 44.8, 45, 53, 59.99, 67, 69.4, 72, 73, 75, 79.9, 85, and/or any value or subrange therebetween. In certain exemplary embodiments, component 4500 can have a diameter 4600. In certain exemplary embodiments, a distance 4620 from a chamber 4050 to component 4500 can be approximately equal to diameter 4600 of component 4500.

FIG. 5 is a flowchart of an exemplary embodiment of a method 5000. At activity 5100, a beamsplitter can be fabricated. The beamsplitter can be fabricated from prisms and/or mirrors and can be coated with one or more reflective substances (e.g., aluminum). The beamsplitter can be adapted to pass a portion of light energy and reflect a portion of the light energy at a predetermined angle. The beamsplitter can comprise at least three light reflection zones. The beamsplitter can be a substantially non-planar beamsplitter adapted to provide at least three distinct zones of light reflection.

At activity 5200, a system comprising the beamsplitter can be assembled. The beamsplitter can be a substantially non-planar beamsplitter. The system can comprise an imaging device, chamber, set of light sources (e.g., LEDs), light controller, diffuser, component, information device, machine vision information device, and/or a movable device and/or system adapted to position the component, etc. The imaging device can be a camera, machine vision device and/or system, etc. The movable device and/or system can be adapted to be automatically controlled by the light controller and/or an information device communicatively coupled to an imaging device associated with the system. A component adapted to be illuminated by the set of light sources can be positioned.

At activity 5300, a first subset of light sources can be illuminated. The first set of light sources can be adapted to illuminate a component via the substantially non-planar beamsplitter. In certain exemplary embodiments, the entire set of light sources can be illuminated. Certain exemplary embodiments can be adapted to cause light energy to pass through a diffuser in a light path between the set of light sources and the beamsplitter. The beamsplitter can be adapted to provide at least three distinct zones of light reflection. Each zone of the three distinct zones of light reflection can be adapted to cause light from the set of light sources to be reflected at a different angle relative to an axis of a camera. The beamsplitter can be adapted to illuminate the component with light energy reflected from each of the three distinct light reflection zones. The beamsplitter can be adapted to provide an increased quantity of light for illumination of the component as compared to a single zone of reflection of a substantially planar beamsplitter.

At activity 5400, a first image of the component can be obtained and/or captured via a camera. A lens of the camera can be facing the component along an axis of the camera. The first image can be obtained via the imaging device and can be automatically provided to a processor and/or information device. The processor and/or information device can be adapted to interpret and/or analyze the first image and/or illumination associated with the first image.

At activity 5500, a second subset of light sources can be determined. For example, the processor and/or information device can be adapted to make a determination of the second subset of light sources based upon the interpretation and/or analysis of the first image and/or illumination associated with the first image. The processor and/or information device can be adapted to examine one or more detected and/or predetermined features of the component and automatically determine if illumination of the component is acceptable. If illumination of the component is not acceptable, the processor and/or information device can be adapted to analyze reflection information and/or shadow information associated with the image in order to automatically determine the second subset of light sources.

At activity 5600, the second subset of light sources can be illuminated. The second set of light sources can be illuminated via a light controller. The light controller can illuminate the second subset of light sources based upon information received from and/or determined by the processor and/or information device.

At activity 5700, a second image of the component can be obtained. The second image can be obtained via the imaging device and can be automatically provided to the processor and/or information device. The processor and/or information device can be adapted to interpret and/or analyze the second image and/or illumination associated with the second image. Based upon an automatic determination of the processor and/or information device, one or more activities of method 5000 can be recursively repeated until an interpretable and/or decodable image of the component is obtained.

Figure 6:
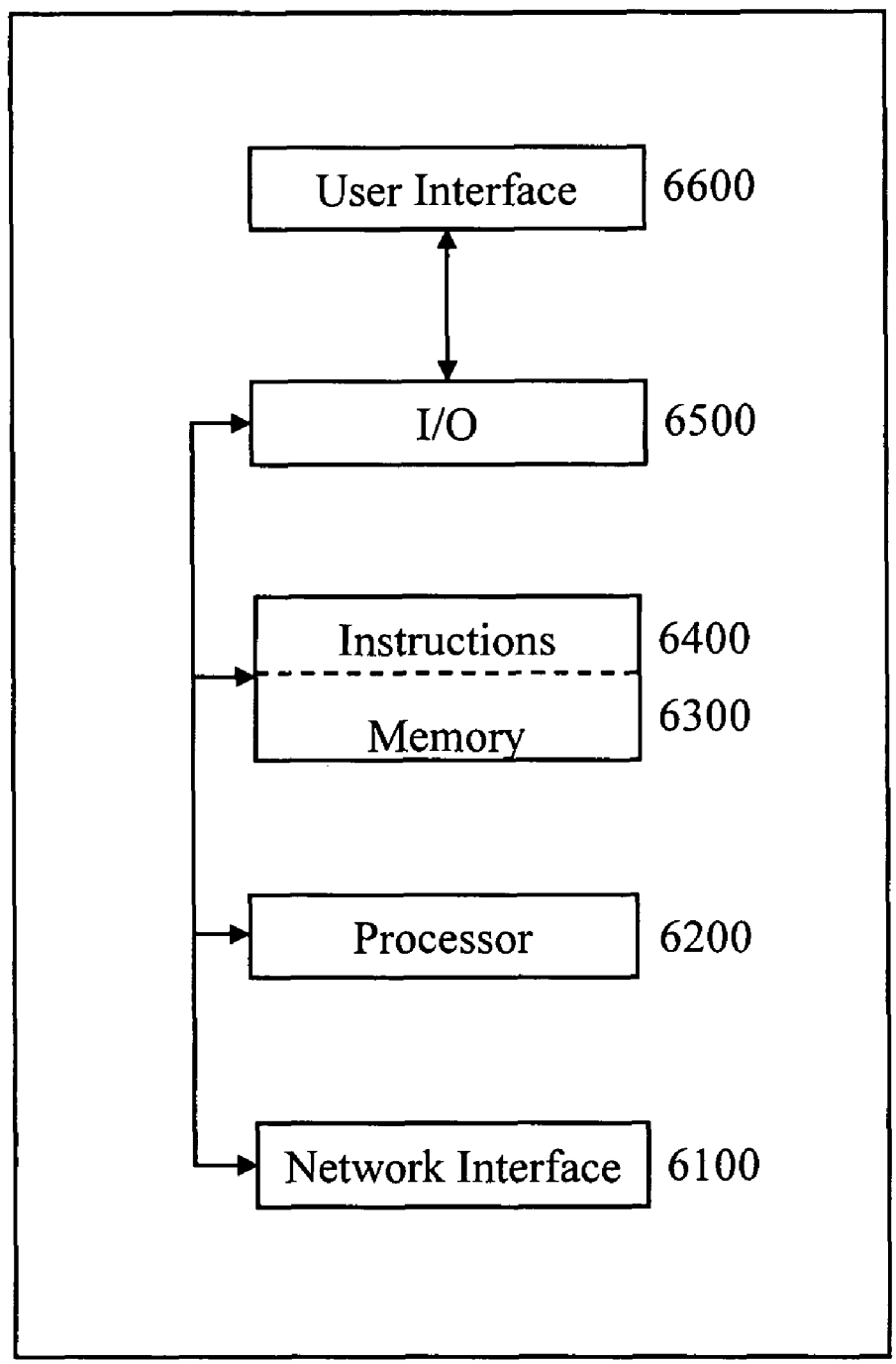
FIG. 6 is a block diagram of an exemplary embodiment of an information device 6000.

FIG. 6 is a block diagram of an exemplary embodiment of an information device 6000, which in certain operative embodiments can comprise, for example, information device 1900, of FIG. 1. Information device 6000 can comprise any of numerous components, such as for example, one or more network interfaces 6100, one or more processors 6200, one or more memories 6300 containing instructions 6400, one or more input/output (I/O) devices 6500, and/or one or more user interfaces 6600 coupled to I/O device 6500, etc.

In certain exemplary embodiments, via one or more user interfaces 6600, such as a graphical user interface, a user can view a rendering of information related to imaging, photographing, researching, designing, modeling, creating, developing, building, manufacturing, operating, maintaining, storing, marketing, selling, delivering, selecting, specifying, requesting, ordering, receiving, returning, rating, and/or recommending any of the products, services, methods, and/or information described herein.

DEFINITIONS

When the following terms are used substantively herein, the accompanying definitions apply. These terms and definitions are presented without prejudice, and, consistent with the application, the right to redefine these terms during the prosecution of this application or any application claiming priority hereto is reserved. For the purpose of interpreting a claim of any patent that claims priority hereto, each definition (or redefined term if an original definition was amended during the prosecution of that patent), functions as a clear and unambiguous disavowal of the subject matter outside of that definition.

a—at least one.

activity—an action, act, deed, function, step, and/or process and/or a portion thereof.

adapted to—suitable, fit, and/or capable of performing a specified function.

adjacent—in close proximity to, near, next to, and/or adjoining.

along—in line with a direction.

and/or—either in conjunction with or in alternative to.

angle—an amount of rotation that separates two intersecting lines and/or rays.

apparatus—an appliance or device for a particular purpose.

approximately—about and/or nearly the same as.

associated with—related to.

at least—not less than.

automatically—acting and/or operating in a manner essentially independent of external human influence and/or control. For example, an automatic light switch can turn on upon "seeing" a person in its view, without the person manually operating the light switch.

axis—a straight line about which a body or geometric object rotates or can be conceived to rotate and/or a center line to which parts of a structure or body can be referred.

based upon—determined in consideration of and/or derived from.

beamsplitter—a device and/or system adapted to of split and/or join a light beam into or from two or more beams that differ in wavelength, polarity, and/or direction.

between—in a separating interval and/or intermediate to.

bottom edge—a lower extent of a beamsplitter oriented substantially upright, the lower extent of the beamsplitter furthest away from the camera in the operative system.

camera—a device often comprising a lightproof enclosure having an aperture with a lens through which a still and/or moving image of an object is focused and recorded on a photosensitive film, plate, tape, and/or or sensor coupled to an electronic and/or optical memory device (e.g., RAM, EEPROM, flash memory, magnetic disk, optical disk, etc.). The aperture with the lens defines an axis of the camera.

can—is capable of, in at least some embodiments.

capable—a potential for use.

capture—to obtain and/or record data in preparation for processing and/or storage.

cause—to bring about, provoke, precipitate, produce, elicit, be the reason for, result in, and/or effect.

chamber—an enclosed space or compartment.

circuit—an electrically conductive pathway and/or a communications connection established across two or more switching devices comprised by a network and between corresponding end systems connected to, but not comprised by the network.

closest—physically and/or logically nearest.

compare—to examine in order to note similarities and/or differences in relation to something else.

component—a constituent element and/or part.

comprised by—included by.

comprise—to include but not be limited to.

control—to direct.

controller—a device and/or set of machine-readable instructions for performing one or more predetermined and/or user-defined tasks. A controller can comprise any one or a combination of hardware, firmware, and/or software. A controller can utilize mechanical, pneumatic, hydraulic, electrical, magnetic, optical, informational, chemical, and/or biological principles, signals, and/or inputs to perform the task(s). In certain embodiments, a controller can act upon information by manipulating, analyzing, modifying, converting, transmitting the information for use by an executable procedure and/or an information device, and/or routing the information to an output device. A controller can be a central processing unit, a local controller, a remote controller, parallel controllers, and/or distributed controllers, etc. The controller can be a general-purpose microcontroller, such the Pentium IV series of microprocessor manufactured by the Intel Corporation of Santa Clara, Calif., and/or the HC08 series from Motorola of Schaumburg, Ill. In another embodiment, the controller can be an Application Specific Integrated Circuit (ASIC) or a Field Programmable Gate Array (FPGA) that has been designed to implement in its hardware and/or firmware at least a part of an embodiment disclosed herein.

cross-section—a section formed by a plane cutting through an object at a right angle to an axis.

curve—to bend continuously substantially without angles.

define—to establish the meaning, relationship, outline, form, and/or structure of; and/or to precisely and/or distinctly describe and/or specify.

design—(n) a purposeful arrangement of parts and/or details. For example, the design of a product and/or process can comprise designing predetermined aspects of the product and/or process. (v) to plan, such as in a manner that comprises the development of a graphic representation.

determine—to obtain, calculate, decide, deduce, establish, and/or ascertain.

device—a machine, manufacture, and/or collection thereof.

diameter—a length of a straight line segment passing through a center of an object and terminating at the periphery thereof.

different—changed, distinct, and/or separate.

diffuser—a substantially translucent structure adapted to expand the diameter of a light source and reduce the effects of focused and/or collimated lighting.

dimension—size.

disposed—placed, arranged, and/or oriented.

distance—a measure of physical and/or logical separation.

distinct—discrete and/or readily distinguishable from all others.

each—every one of a group considered individually.

emit—to give off, send forth, and/or discharge.

energy—usable power.

equal—substantially the same as.

face—to be oriented in a direction of.

first—an initial entity in an ordering.

flow—a continuous transfer.

for—with a purpose of.

from—used to indicate a source.

further—in addition.

greater than—larger in magnitude.

have—to be identified by.

height—a distance from a point at a given level to a point at a different level.

illuminate—to light and/or cause light to be incident thereon.

image—an at least two-dimensional representation of an entity and/or phenomenon.

increase—to become greater or more in size, quantity, number, degree, value, intensity, and/or power, etc.

in excess of—greater than.

information—facts, terms, concepts, phrases, expressions, commands, numbers, characters, and/or symbols, etc., that are related to a subject. Sometimes used synonymously with data, and sometimes used to describe organized, transformed, and/or processed data. It is generally possible to automate certain activities involving the management, organization, storage, transformation, communication, and/or presentation of information.

information device—any device on which resides a finite state machine capable of implementing at least a portion of a method, structure, and/or or graphical user interface described herein. An information device can comprise well-known communicatively coupled components, such as one or more network interfaces, one or more processors, one or more memories containing instructions, one or more input/output (I/O) devices, and/or one or more user interfaces (e.g., coupled to an I/O device) via which information can be rendered to implement one or more functions described herein. For example, an information device can be any general purpose and/or special purpose computer, such as a personal computer, video game system (e.g., PlayStation, Nintendo Gameboy, X-Box, etc.), workstation, server, minicomputer, mainframe, supercomputer, computer terminal, laptop, wearable computer, and/or Personal Digital Assistant (PDA), ipod, mobile terminal, Bluetooth device, communicator, "smart" phone (such as a Treo-like device), messaging service (e.g., Blackberry) receiver, pager, facsimile, cellular telephone, a traditional telephone, telephonic device, a programmed microprocessor or microcontroller and/or peripheral integrated circuit elements, a digital signal processor, an ASIC or other integrated circuit, a hardware electronic logic circuit such as a discrete element circuit, and/or a programmable logic device such as a PLD, PLA, FPGA, or PAL, or the like, etc.

instructions—directions adapted to perform a particular operation or function. Can be implemented as firmware and/or software.

interpret—to make sense of and/or assign a meaning to.

input/output (I/O) device—any sensory-oriented input and/or output device, such as an audio, visual, haptic, olfactory, and/or taste-oriented device, including, for example, a monitor, display, projector, overhead display, keyboard, keypad, mouse, trackball, joystick, gamepad, wheel, touchpad, touch panel, pointing device, microphone, speaker, video camera, camera, scanner, printer, haptic device, vibrator, tactile simulator, and/or tactile pad, potentially including a port to which an I/O device can be attached or connected.

lens—a piece of transparent substance, usually glass, having two opposite surfaces either both curved or one curved and one plane, used in an optical device for changing the convergence and/or focal point of light rays.

light—(n) a device and/or system adapted to provide illumination; (v) to provide electromagnetic radiation to which organs of sight react, ranging in wavelength from approximately 300 to approximately 1000 nm.

light controller—a controller that is adapted to cause an illumination of one or more light sources and/or adapted to provide intensity control of each light source.

light emitting diode (LED)—a semiconductor device that emits (typically visible) light responsive to an applied electrical conducting current.

light reflection zone—a defined portion of a beamsplitter adapted to reflect light at a predetermined angle.

light source—a device and/or system adapted to provide illumination responsive to applied electrical energy.

located—situated in a particular spot and/or position.

machine instructions—directions adapted to cause a machine, such as an information device, to perform one or more particular activities, operations, and/or functions. The directions, which can sometimes form an entity called a "processor", "kernel", "operating system", "program", "application", "utility", "subroutine", "script", "macro", "file", "project", "module", "library", "class", and/or "object", etc., can be embodied as machine code, source code, object code, compiled code, assembled code, interpretable code, and/or executable code, etc., in hardware, firmware, and/or software.

machine-readable—capable of being discerned by an information device.

machine-readable medium—a physical structure from which a machine, such as an information device, computer, microprocessor, and/or controller, etc., can obtain and/or store data, information, and/or instructions. Examples include memories, punch cards, and/or optically-readable forms, etc.

machine vision—devices and/or systems adapted to use video cameras, robots, other devices, and/or computers to obtain and/or analyze visual and/or video information pertaining to an operation or activity.

may—is allowed and/or permitted to, in at least some embodiments.

memory device—an apparatus capable of storing analog or digital information, such as instructions and/or data. Examples include a non-volatile memory, volatile memory, Random Access Memory, RAM, Read Only Memory, ROM, flash memory, magnetic media, a hard disk, a floppy disk, a magnetic tape, an optical media, an optical disk, a compact disk, a CD, a digital versatile disk, a DVD, and/or a raid array, etc. The memory device can be coupled to a processor and/or can store instructions adapted to be executed by processor, such as according to an embodiment disclosed herein.

method—a process, procedure, and/or collection of related activities for accomplishing something.

more—a quantifier meaning greater in size, amount, extent, and/or degree.

mount—(n) that upon which a thing is attached. (v) to couple, fix, and/or attach on and/or to something.

network—a communicatively coupled plurality of nodes. A network can be and/or utilize any of a wide variety of sub-networks, such as a circuit switched, public-switched, packet switched, data, telephone, telecommunications, video distribution, cable, terrestrial, broadcast, satellite, broadband, corporate, global, national, regional, wide area, backbone, packet-switched TCP/IP, Fast Ethernet, Token Ring, public Internet, private, ATM, multi-domain, and/or multi-zone sub-network, one or more Internet service providers, and/or one or more information devices, such as a switch, router, and/or gateway not directly connected to a local area network, etc.

network interface—any device, system, or subsystem capable of coupling an information device to a network. For example, a network interface can be a telephone, cellular phone, cellular modem, telephone data modem, fax modem, wireless transceiver, Ethernet card, cable modem, digital subscriber line interface, bridge, hub, router, or other similar device.

non—not.

obtain—to receive, get, take possession of, procure, acquire, calculate, determine, and/or compute.

one—a single unit.

operative—being in effect; operating.

pair—a quantity of two of something.

pass—to convey, transfer, and/or transmit.

path—a route along which something moves.

photograph—to record an image.

planar—shaped as a substantially flat two-dimensional surface.

plane—a substantially flat surface.

plurality—the state of being plural and/or more than one.

portion—a part, component, section, percentage, ratio, and/or quantity that is less than a larger whole. Can be visually, physically, and/or virtually distinguishable and/or non-distinguishable.

position—to put in place.

predetermined—established in advance.

prevent—to impede, hinder, stop, and/or keep from happening.

processor—a device and/or set of machine-readable instructions for performing one or more predetermined tasks. A processor can comprise any one or a combination of hardware, firmware, and/or software. A processor can utilize mechanical, pneumatic, hydraulic, electrical, magnetic, optical, informational, chemical, and/or biological principles, signals, and/or inputs to perform the task(s). In certain embodiments, a processor can act upon information by manipulating, analyzing, modifying, converting, transmitting the information for use by an executable procedure and/or an information device, and/or routing the information to an output device. A processor can function as a central processing unit, local controller, remote controller, parallel controller, and/or distributed controller, etc. Unless stated otherwise, the processor can be a general-purpose device, such as a microcontroller and/or a microprocessor, such the Pentium IV series of microprocessor manufactured by the Intel Corporation of Santa Clara, Calif. In certain embodiments, the processor can be dedicated purpose device, such as an Application Specific Integrated Circuit (ASIC) or a Field Programmable Gate Array (FPGA) that has been designed to implement in its hardware and/or firmware at least a part of an embodiment disclosed herein.

provide—to furnish, supply, give, convey, send, and/or make available.

quantity—a specified amount and/or measure.

receive—to gather, take, acquire, obtain, accept, get, and/or have bestowed upon.

rectangular—defined by four substantially right angles.

reflect—to bounce back from a surface.

regarding—pertaining to.

relative—considered with reference to and/or in comparison to something else.

render—to make perceptible to a human, for example as data, commands, text, graphics, audio, video, animation, and/or hyperlinks, etc., such as via any visual, audio, and/or haptic means, such as via a display, monitor, electric paper, ocular implant, cochlear implant, speaker, etc.

said—when used in a system or device claim, an article indicating a subsequent claim term that has been previously introduced.

second—an entity immediately following a first entity in an ordering.

segregate—to separate.

set—a related plurality of predetermined elements; and/or one or more distinct items and/or entities having a specific common property or properties.

shape—a characteristic surface, outline, and/or contour of an entity.

signal—information, such as machine instructions for activities, encoded as automatically detectable variations in a physical variable, such as a pneumatic, hydraulic, acoustic, fluidic, mechanical, electrical, magnetic, optical, chemical, and/or biological variable, such as power, energy, pressure, flowrate, viscosity, density, torque, impact, force, voltage, current, resistance, magnetomotive force, magnetic field intensity, magnetic field flux, magnetic flux density, reluctance, permeability, index of refraction, optical wavelength, polarization, reflectance, transmittance, phase shift, concentration, and/or temperature, etc. Depending on the context, a signal can be synchronous, asynchronous, hard real-time, soft real-time, non-real time, continuously generated, continuously varying, analog, discretely generated, discretely varying, quantized, digital, continuously measured, and/or discretely measured, etc.

simultaneously—at substantially the same time.

single—existing alone or consisting of one entity.

size—physical dimensions, proportions, magnitude, amount, and/or extent of an entity.

subset—a portion of a set.

substantially—to a considerable, large, and/or great, but not necessarily whole and/or entire, extent and/or degree.

system—a collection of mechanisms, devices, data, and/or instructions, the collection designed to perform one or more specific functions.

three—one plus one plus one.

through—in one side and out another side of.

transmit—to send as a signal, provide, furnish, and/or supply.

turn on—to put into operation and/or activate.

two times—approximately two times in magnitude.

user interface—any device for rendering information to a user and/or requesting information from the user. A user interface includes at least one of textual, graphical, audio, video, animation, and/or haptic elements. A textual element can be provided, for example, by a printer, monitor, display, projector, etc. A graphical element can be provided, for example, via a monitor, display, projector, and/or visual indication device, such as a light, flag, beacon, etc. An audio element can be provided, for example, via a speaker, microphone, and/or other sound generating and/or receiving device. A video element or animation element can be provided, for example, via a monitor, display, projector, and/or other visual device. A haptic element can be provided, for example, via a very low frequency speaker, vibrator, tactile stimulator, tactile pad, simulator, keyboard, keypad, mouse, trackball, joystick, gamepad, wheel, touchpad, touch panel, pointing device, and/or other haptic device, etc. A user interface can include one or more textual elements such as, for example, one or more letters, number, symbols, etc. A user interface can include one or more graphical elements such as, for example, an image, photograph, drawing, icon, window, title bar, panel, sheet, tab, drawer, matrix, table, form, calendar, outline view, frame, dialog box, static text, text box, list, pick list, pop-up list, pull-down list, menu, tool bar, dock, check box, radio button, hyperlink, browser, button, control, palette, preview panel, color wheel, dial, slider, scroll bar, cursor, status bar, stepper, and/or progress indicator, etc. A textual and/or graphical element can be used for selecting, programming, adjusting, changing, specifying, etc. an appearance, background color, background style, border style, border thickness, foreground color, font, font style, font size, alignment, line spacing, indent, maximum data length, validation, query, cursor type, pointer type, autosizing, position, and/or dimension, etc. A user interface can include one or more audio elements such as, for example, a volume control, pitch control, speed control, voice selector, and/or one or more elements for controlling audio play, speed, pause, fast forward, reverse, etc. A user interface can include one or more video elements such as, for example, elements controlling video play, speed, pause, fast forward, reverse, zoom-in, zoom-out, rotate, and/or tilt, etc. A user interface can include one or more animation elements such as, for example, elements controlling animation play, pause, fast forward, reverse, zoom-in, zoom-out, rotate, tilt, color, intensity, speed, frequency, appearance, etc. A user interface can include one or more haptic elements such as, for example, elements utilizing tactile stimulus, force, pressure, vibration, motion, displacement, temperature, etc.

utilize—to use and/or put into service.

via—by way of and/or utilizing.

viewing aperture—an opening of a camera lens that is usable in viewing a component.

wherein—in regard to which; and; and/or in addition to.

which—what particular one or ones.

width—a measurement of the extent of something along a dimension.

with—accompanied by.

without—not accompanied by.

zone—an area and/or region distinguished from adjacent parts by a distinctive feature and/or characteristic.

Note

Still other substantially and specifically practical and useful embodiments will become readily apparent to those skilled in this art from reading the above-recited and/or herein-included detailed description and/or drawings of certain exemplary embodiments. It should be understood that numerous variations, modifications, and additional embodiments are possible, and accordingly, all such variations, modifications, and embodiments are to be regarded as being within the scope of this application.

Thus, regardless of the content of any portion (e.g., title, field, background, summary, abstract, drawing figure, etc.) of this application, unless clearly specified to the contrary, such as via an explicit definition, assertion, or argument, with respect to any claim, whether of this application and/or any claim of any application claiming priority hereto, and whether originally presented or otherwise:

there is no requirement for the inclusion of any particular described or illustrated characteristic, function, activity, or element, any particular sequence of activities, or any particular interrelationship of elements;

any elements can be integrated, segregated, and/or duplicated;

any activity can be repeated, performed by multiple entities, and/or performed in multiple jurisdictions; and any activity or element can be specifically excluded, the sequence of activities can vary, and/or the interrelationship of elements can vary.

Moreover, when any number or range is described herein, unless clearly stated otherwise, that number or range is approximate. When any range is described herein, unless clearly stated otherwise, that range includes all values therein and all subranges therein. For example, if a range of 1 to 10 is described, that range includes all values therebetween, such as for example, 1.1, 2.5, 3.335, 5, 6.179, 8.9999, etc., and includes all subranges therebetween, such as for example, 1 to 3.65, 2.8 to 8.14, 1.93 to 9, etc.

Any information in any material (e.g., a United States patent, United States patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

Accordingly, every portion (e.g., title, field, background, summary, abstract, drawing figure, etc.) of this application, other than the claims themselves, is to be regarded as illustrative in nature, and not as restrictive.

What is claimed is:

1. A beamsplitter comprising:

a substantially planar first reflection zone positioned such that its normal is at an angle relative to an optical axis, wherein light incident on the beamsplitter at an incidence angle relative to the normal is reflected by the first reflection zone toward an object at a first angle relative to the optical axis and wherein the first reflection zone is an imaging portion of the beamsplitter that transmits light reflected from the object substantially without optical distortion; and one or more additional reflection zones coupled to the first reflection zone, wherein each of the one or more additional reflection zones reflects light incident on the beam splitter at the incidence angle toward the object at an angle relative to the optical axis that is different than the first angle.

2. The beamsplitter of claim 1 wherein the angle between the normal and the optical axis is approximately 45 degrees.

3. The beamsplitter of claim 1 wherein the one or more additional reflection zones comprise:

a second reflection zone coupled to one end of the first reflection zone; and a third reflection zone coupled to the opposite end of the first reflection zone.

4. The beamsplitter of claim 3 wherein the second and third reflection zones are substantially planar.

5. The beamsplitter of claim 4 wherein second reflection zone and the third reflection zone are positioned such that their normals are at an angle relative to the normal of the first reflection zone.

6. The beamsplitter of claim 3 wherein the second and third reflection zones are non-planar.

7. An illuminator comprising:

one or more individually controllable light sources;

a beamsplitter optically coupled to the plurality of individually controllable light sources, the beamsplitter comprising:
  a substantially planar first reflection zone positioned such that its normal is at an angle relative to an optical axis, wherein light incident on the beamsplitter at an incidence angle relative to the normal is reflected by the first reflection zone toward an object at a first angle relative to the optical axis and wherein the first reflection zone is an imaging portion of the beamsplitter that transmits light reflected from the object substantially without optical distortion, and
  one or more additional reflection zones coupled to the first reflection zone, wherein each of the one or more additional reflection zones reflects light incident on the beam splitter at the incidence angle toward the object at an angle relative to the optical axis that is different than the first angle; and
circuitry and logic for selectively activating one or more of the one or more individually controllable light sources to change the illumination provided by the illuminator.

8. The illuminator of claim 7 wherein each of the one or more controllable light sources comprises:
one or more sources; and
a diffuser optically coupled to the one or more sources.

9. The illuminator of claim 8 wherein the one or more sources comprises light emitting diodes (LEDs), incandescent bulbs, or fiber optically transmitted light sources.

10. The illuminator of claim 7 wherein each of the one or more controllable light sources comprises an electroluminescent strip.

11. The illuminator of claim 7 wherein the one or more additional reflection zones comprise a second reflection zone and a third reflection zone, and wherein the second reflection zone and the third reflection zone are substantially planar and are positioned such that their normals are at an angle relative to the normal of the first reflection zone.

12. The illuminator of claim 7 wherein the one or more additional reflection zones comprise non-planar second and third reflection zones.

13. The illuminator of claim 7 wherein selectively activating one or more of the one or more individually controllable light sources comprises changing the brightness of at least one of the one or more individually controllable light sources.

14. The illuminator of claim 7 wherein selectively activating one or more of the one or more individually controllable light sources comprises activating or deactivating at least one of the one or more individually controllable light sources.

15. An imaging system comprising:
a camera having an optical axis;
an illuminator positioned along the optical axis, the illuminator comprising:
  one or more individually controllable diffuse light sources;
  a beamsplitter optically coupled to the one or more individually controllable light sources, the beamsplitter comprising:
    a substantially planar first reflection zone positioned such that its normal is at an angle relative to an optical axis, wherein light incident on the beamsplitter at an incidence angle relative to the normal is reflected by the first reflection zone toward an object at a first angle relative to the optical axis and wherein the first reflection zone is an imaging portion of the beamsplitter that transmits light reflected from the object substantially without optical distortion, and
    one or more additional reflection zones coupled to the first reflection zone, wherein each of the one or more additional reflection zones reflect light incident on the beam splitter at the incidence angle toward the object at an angle relative to the optical axis that is different than the first angle; and
a processor coupled to the illuminator and to the camera.

16. The imaging system of claim 15 wherein each of the one or more controllable light sources comprises:
one or more sources; and
a diffuser optically coupled to the one or more sources.

17. The imaging system of claim 16 wherein the one or more sources can comprise light emitting diodes (LEDs), incandescent bulbs, or fiber optically transmitted light sources.

18. The imaging system of claim 15 wherein each of the one or more controllable light sources comprises an electroluminescent strip.

19. The imaging system of claim 15 wherein the one or more additional reflection zones comprise a second reflection zone and a third reflection zone, and wherein the second reflection zone and the third reflection zone are substantially planar and are positioned such that their normals are at an angle relative to the normal of the first reflection zone.

20. The imaging system of claim 15 wherein the one or more additional reflection zones comprise non-planar second and third reflection zones.

21. The imaging system of claim 15 wherein the processor is coupled to the illuminator and to the camera through a network.

22. The imaging system of claim 15, further comprising a light controller coupled between the processor and the one or more individually controllable light sources.

23. The imaging system of claim 22 wherein the light controller changes the brightness of at least one of the one or more individually controllable light sources in response to images obtained by the camera.

24. The imaging system of claim 22 wherein the light controller activates or deactivates at least one of the one or more individually controllable light sources in response to images obtained by the camera.

25. The imaging system of claim 15, further comprising a storage device coupled to the processor.

26. A process for illuminating an object, the process comprising:
directing light from one or more light sources toward a beamsplitter, the beamsplitter comprising:
  a substantially planar first reflection zone positioned such that its normal is at an angle relative to an optical axis, wherein light incident on the beamsplitter at an incidence angle relative to the normal is reflected by the first reflection zone toward the object at a first angle relative to the optical axis, and
  one or more additional reflection zones coupled to the first reflection zone, wherein each of the one or more additional reflection zones reflect light incident on the beam splitter at the incidence angle toward the object at an angle relative to the optical axis that is different than the first angle; and
capturing an image of the object through the first reflection zone.

27. The process of claim 26 wherein the angle between the normal and the optical axis is approximately 45 degrees.

28. The process of claim 26 wherein the one or more additional reflection zones comprise a second reflection zone and a third reflection zone, and wherein the second reflection zone and the third reflection zone are substantially planar and are positioned such that their normals are at an angle relative to the normal of the first reflection zone.

29. The process of claim 26 wherein the one or more additional reflection zones comprise non-planar second and third reflection zones.

30. The process of claim 26, further comprising transmitting the image to a processor for analysis.

31. The process of claim 30, further comprising selectively changing the light directed toward the beamsplitter in response to an analysis of the captured image.

32. The process of claim 31 wherein the one or more light sources are individually controllable, and wherein selectively changing the light directed at the beamsplitter comprises changing the brightness of at least one of the one or more individually controllable light sources.

33. The process of claim 31 wherein the one or more light sources are individually controllable, and wherein selectively changing the light directed at the beamsplitter comprises activating or deactivating at least one of the one or more individually controllable light sources.

34. The process of claim 31, further comprising diffusing the light before directing it toward the beamsplitter.

35. A process for imaging an object, the process comprising:
   positioning the object along the optical axis of a camera;
   positioning an illuminator along the optical axis, the illuminator comprising:
      one or more individually controllable light sources;
      a beamsplitter optically coupled to the one or more individually controllable light sources, the beamsplitter comprising:
         a substantially planar first reflection zone positioned such that its normal is at an angle relative to the optical axis, wherein light incident on the beamsplitter at an incidence angle relative to the normal is reflected by the first reflection zone toward the object at a first angle relative to the optical axis and wherein the first reflection zone is an imaging portion of the beamsplitter that transmits light reflected from the object substantially without optical distortion; and
         one or more additional reflection zones coupled to the first reflection zone, wherein each of the one or more additional reflection zones reflects light incident on the beam splitter at the incidence angle toward the object at an angle relative to the optical axis that is different than the first angle; and
   capturing an image of the object through the first reflection zone.

36. The process of claim 35 wherein the angle between the normal and the optical axis is approximately 45 degrees.

37. The process of claim 35 wherein the one or more additional reflection zones comprise a second reflection zone and a third reflection zone, and wherein the second reflection zone and the third reflection zone are substantially planar and are positioned such that their normals are at an angle relative to the normal of the first reflection zone.

38. The process of claim 35 wherein the one or more additional reflection zones comprise non-planar second and third reflection zones.

39. The process of claim 35, further comprising capturing an image of the object through the first reflection zone.

40. The process of claim 39, further comprising transmitting the image to a processor for analysis.

41. The process of claim 40, further comprising storing the image in a storage device coupled to the processor.

42. The process of claim 40, further comprising selectively changing the output of the light sources in response to an analysis of the captured image.

43. The process of claim 42 wherein selectively changing output of the light sources comprises changing the brightness of at least one of the one or more individually controllable light sources.

44. The process of claim 42 wherein selectively changing the output of the light sources comprises activating or deactivating at least one of the one or more individually controllable light sources.

45. The process of claim 35, further comprising diffusing the light before directing it toward the beamsplitter.

* * * * *